(12) United States Patent
Nishida

(10) Patent No.: US 10,751,502 B2
(45) Date of Patent: Aug. 25, 2020

(54) BODY PILLOW AND VIDEO COMMUNICATION SYSTEM

(71) Applicant: NETAPPLI CO., LTD., Kahoku-gun, Ishikawa (JP)

(72) Inventor: Makoto Nishida, Ishikawa (JP)

(73) Assignee: NETAPPLI CO., LTD., Ishikawa (JP)

( * ) Notice: Subject to any disclaimer, the term of this patent is extended or adjusted under 35 U.S.C. 154(b) by 24 days.

(21) Appl. No.: 16/311,634

(22) PCT Filed: Jun. 20, 2017

(86) PCT No.: PCT/JP2017/022620
§ 371 (c)(1),
(2) Date: Dec. 19, 2018

(87) PCT Pub. No.: WO2017/221915
PCT Pub. Date: Dec. 28, 2017

(65) Prior Publication Data
US 2019/0184132 A1    Jun. 20, 2019

(30) Foreign Application Priority Data

Jun. 21, 2016  (JP) ................................ 2016-122561

(51) Int. Cl.
*A61M 21/00* (2006.01)
*A61H 19/00* (2006.01)
*A47G 9/10* (2006.01)
*H04N 7/14* (2006.01)
*A47C 20/02* (2006.01)
(Continued)

(52) U.S. Cl.
CPC ............. *A61M 21/00* (2013.01); *A47C 20/02* (2013.01); *A47G 9/1027* (2013.01);
(Continued)

(58) Field of Classification Search
CPC ....... A61M 21/00–02; A61H 19/00–50; A61H 23/00–06; A61H 2201/0134–0149; A47G 9/1045–1072; A47G 9/10–109
See application file for complete search history.

(56) References Cited

U.S. PATENT DOCUMENTS

| 6,368,268 B1 | 4/2002 | Sandvick et al. |
| 2010/0174257 A1 | 7/2010 | Matsuura |
(Continued)

FOREIGN PATENT DOCUMENTS

| JP | 2000154481 A | 6/2000 |
| JP | 2002540864 A | 12/2002 |
(Continued)

OTHER PUBLICATIONS

A Decision to Grant a Patent issued by Japanese Patent Office, dated Aug. 17, 2016, for counterpart Japanese application No. 2016-122561. (3 pages).
(Continued)

*Primary Examiner* — Thaddeus B Cox
(74) *Attorney, Agent, or Firm* — Law Office of Katsuhiro Arai

(57) ABSTRACT

In an exemplary embodiment, a body pillow 1 includes: a cushion part 10 of hollow construction made of a transparent and flexible material; leg parts 20 extending downward from the bottom face of the cushion part to create an air flow passage S underneath the bottom face; and affixing means 40 for affixing video playback devices 30 to the bottom face of the cushion part with their video display surfaces 31 facing up. The body pillow has video playback devices provided on the bottom face of a transparent cushion part, so the user can view a video in various postures such as lying face down, face up, or sideways.

20 Claims, 13 Drawing Sheets

(51) Int. Cl.
*H04N 5/64* (2006.01)
*H04N 7/18* (2006.01)
*A47G 9/00* (2006.01)

(52) U.S. Cl.
CPC ......... *A47G 9/1045* (2013.01); *A47G 9/1054* (2013.01); *A61H 19/00* (2013.01); *A61H 19/30* (2013.01); *A61H 19/32* (2013.01); *H04N 5/64* (2013.01); *H04N 7/142* (2013.01); *H04N 7/147* (2013.01); *H04N 7/183* (2013.01); *A47G 2009/008* (2013.01); *A61H 2201/0134* (2013.01); *A61H 2201/10* (2013.01); *A61H 2201/1654* (2013.01); *A61H 2203/0443* (2013.01); *A61H 2205/087* (2013.01); *A61M 2021/005* (2013.01); *A61M 2205/3306* (2013.01); *A61M 2205/583* (2013.01); *A61M 2205/59* (2013.01); *A61M 2230/63* (2013.01)

(56) References Cited

U.S. PATENT DOCUMENTS

2015/0342377 A1\* 12/2015 Hall ...................... A47G 9/1045
　　　　　　　　　　　　　　　　　　　　　　　　　　　345/156
2016/0324343 A1\* 11/2016 Sherwin .................... B32B 7/05

FOREIGN PATENT DOCUMENTS

| | | | |
|---|---|---|---|
| JP | 2008515584 | A | 5/2008 |
| JP | 2008521070 | A | 6/2008 |
| JP | 2008148774 | A | 7/2008 |
| JP | 5260866 | B2 | 8/2013 |
| JP | 5261382 | B2 | 8/2013 |
| JP | 2015039622 | A | 3/2015 |
| JP | 3197671 | U | 5/2015 |
| JP | 2016016032 | A | 2/2016 |
| WO | 0059581 | A1 | 10/2000 |
| WO | 2006030407 | A1 | 3/2006 |
| WO | 2006040751 | A1 | 4/2006 |
| WO | 2008149883 | A1 | 12/2008 |

OTHER PUBLICATIONS

International Search Report (ISR) dated Aug. 1, 2017, issued for International application No. PCT/JP2017/022620.
White Hands, Inc., Solving the Issue of Sexual Needs of Disabled Persons, http://www.whitehands.jp/disability.html, Retrieved on Dec. 5, 2018.

\* cited by examiner

[FIG. 1]
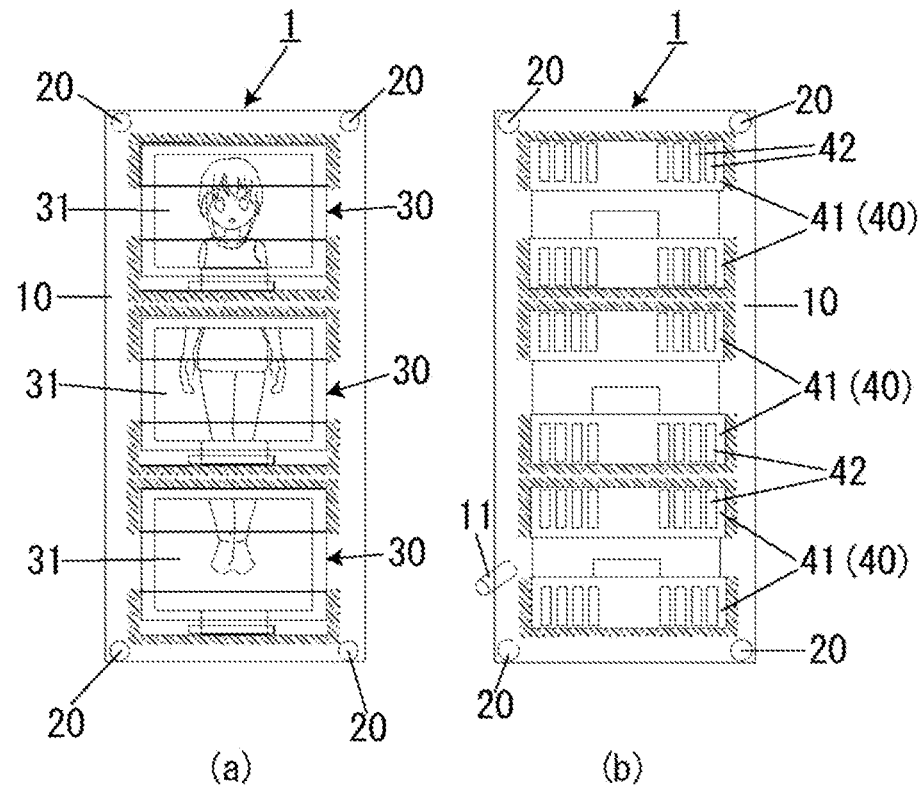
[FIG. 2]
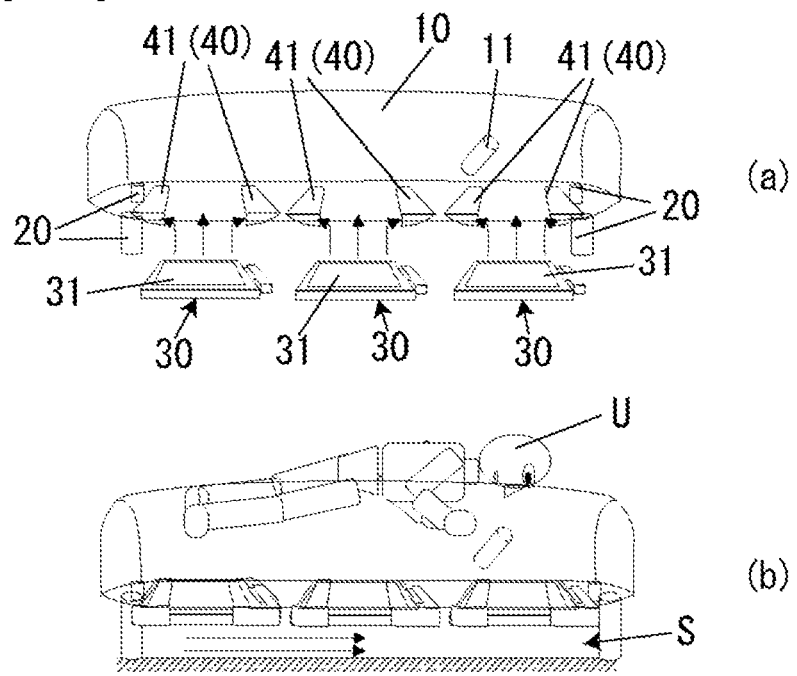

[FIG. 3]
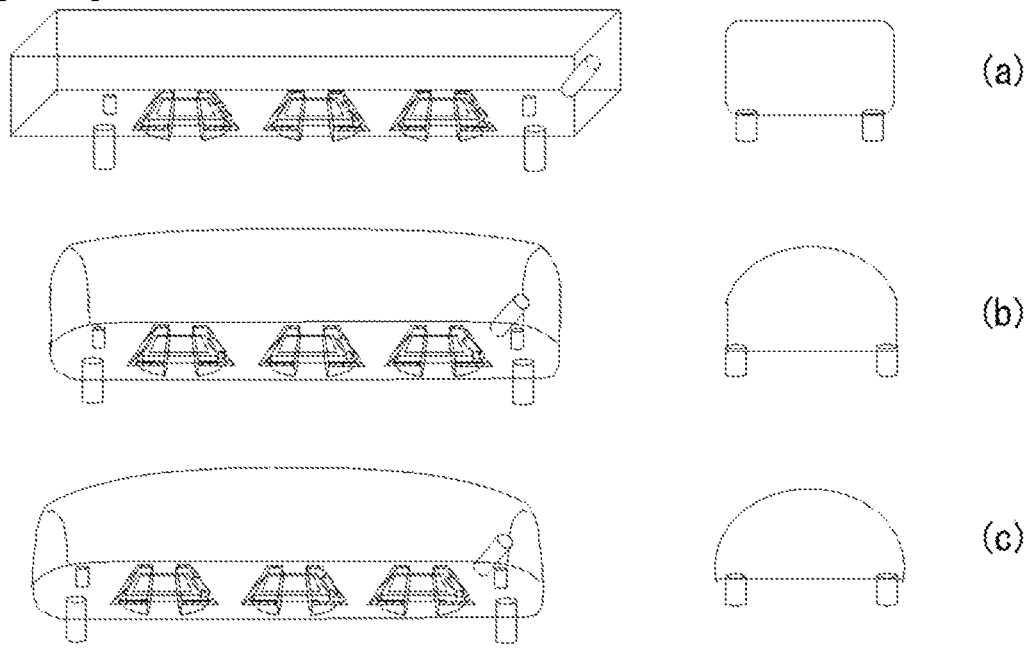
[FIG. 4]
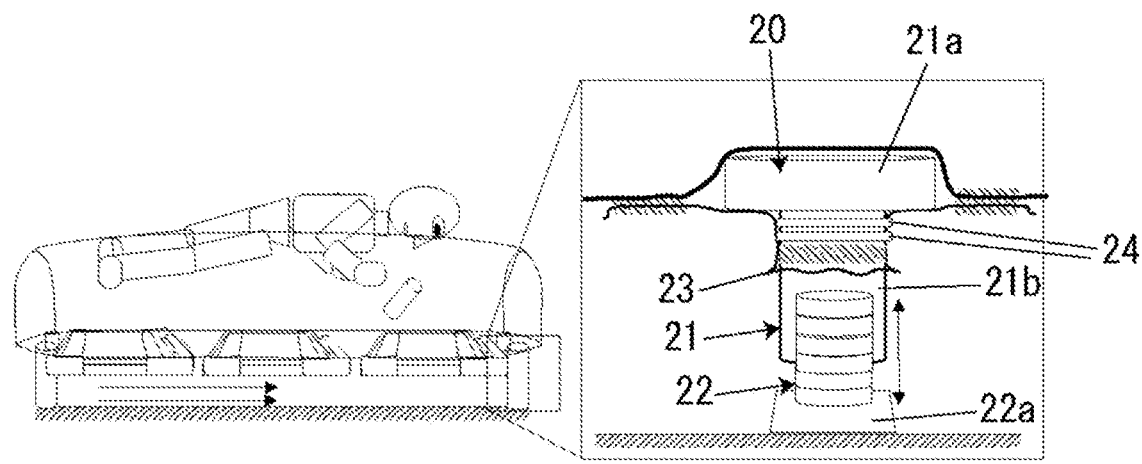
[FIG. 5]
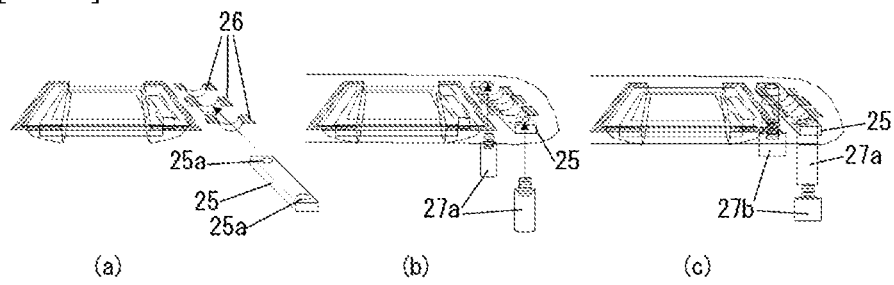

[FIG. 6]
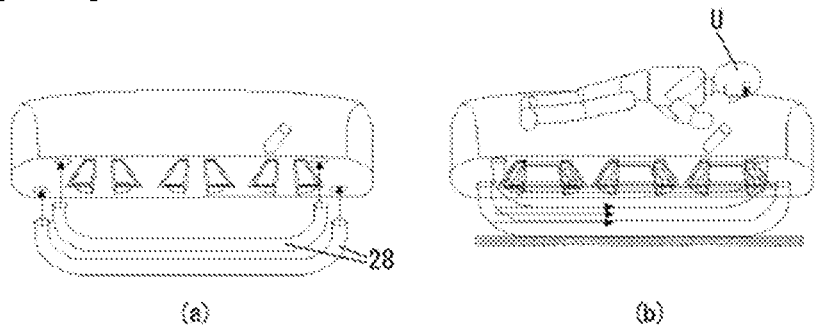
[FIG. 7]
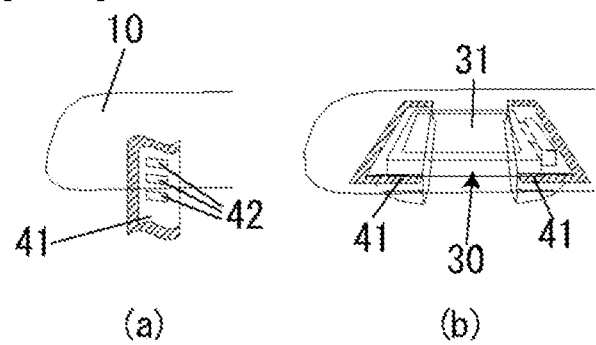
[FIG. 8]
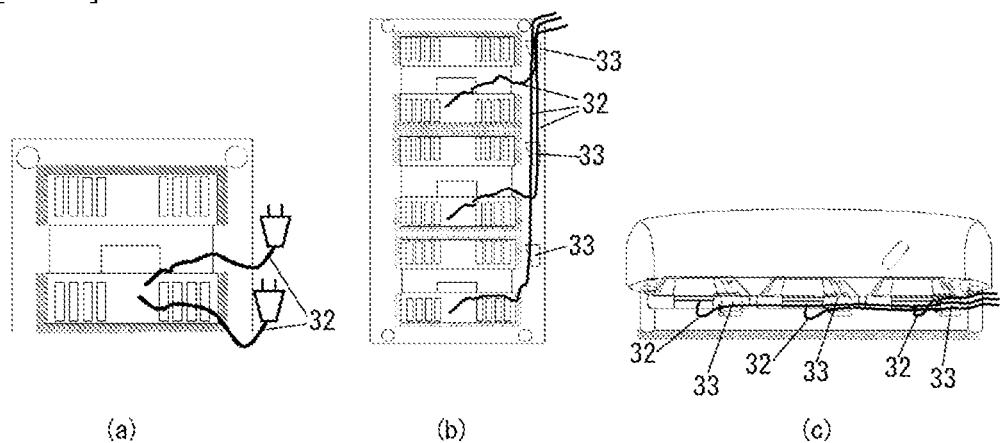
[FIG. 9]
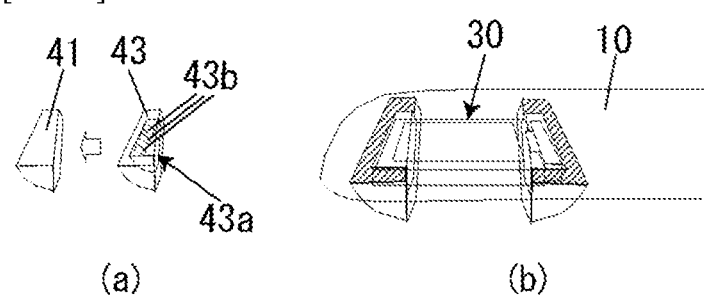

[FIG. 10]
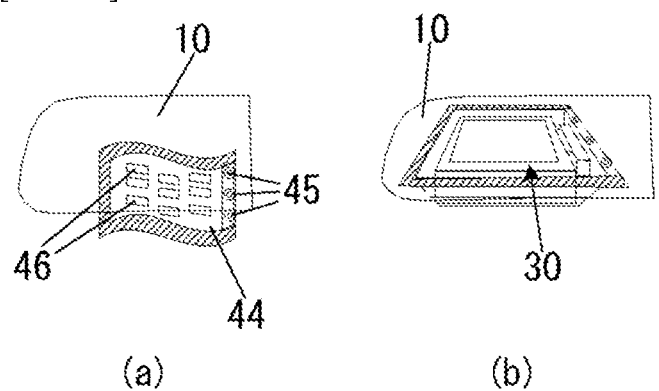
[FIG. 11]
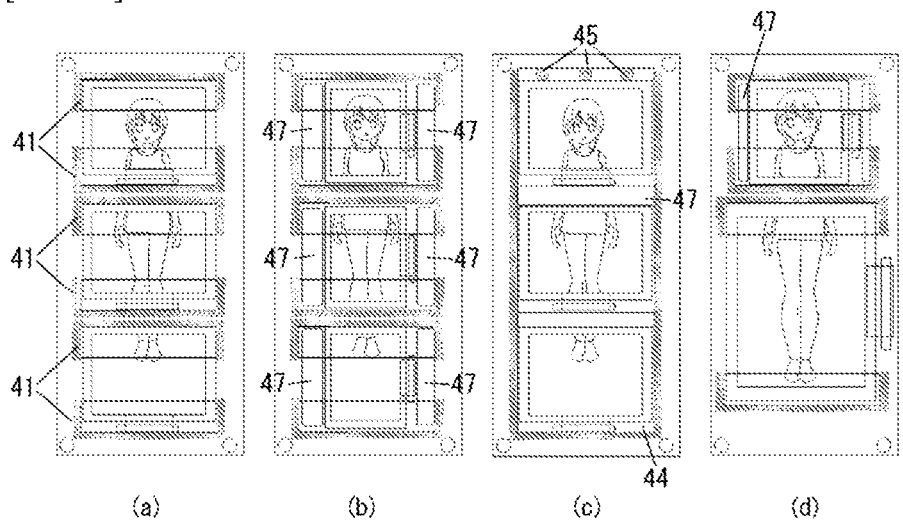
[FIG. 12]
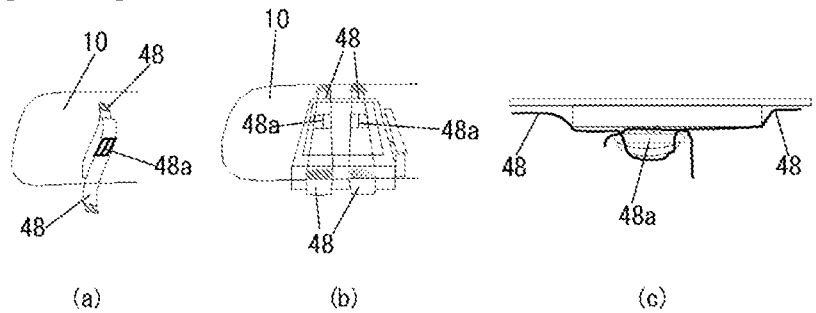

[FIG. 13]
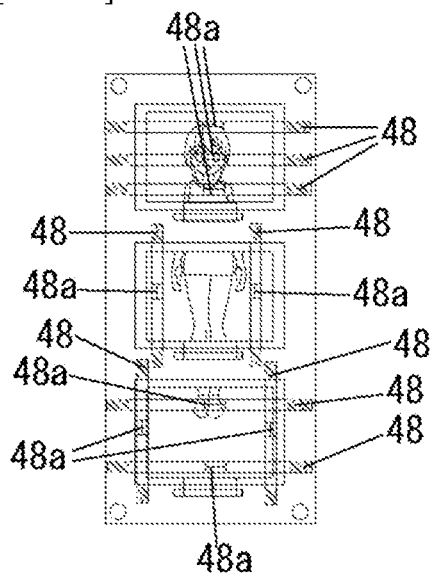
[FIG. 14]
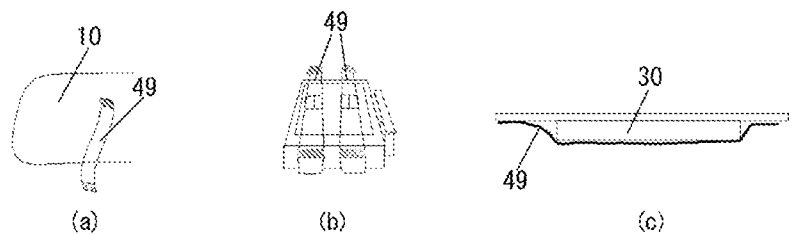
[FIG. 15]
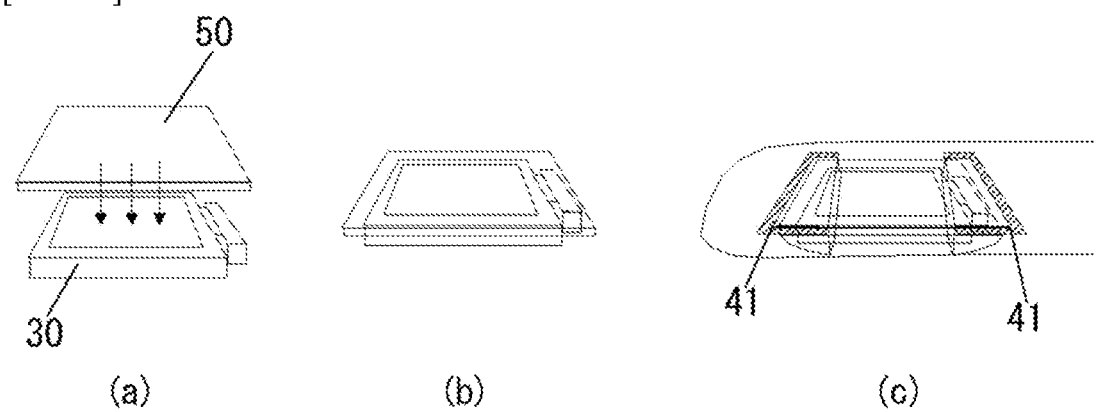
[FIG. 16]
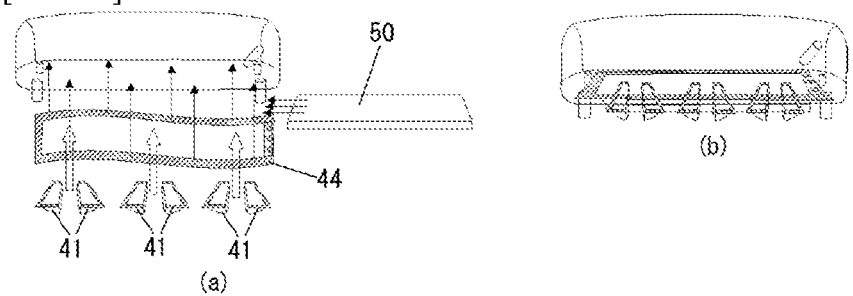

[FIG. 17]
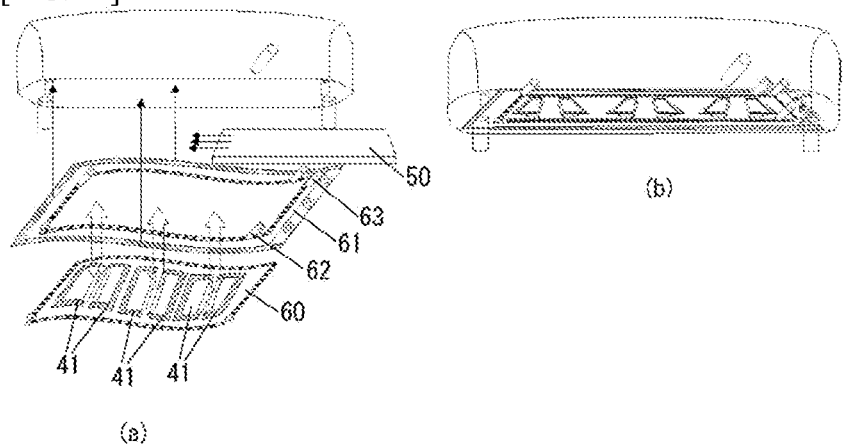
[FIG. 18]
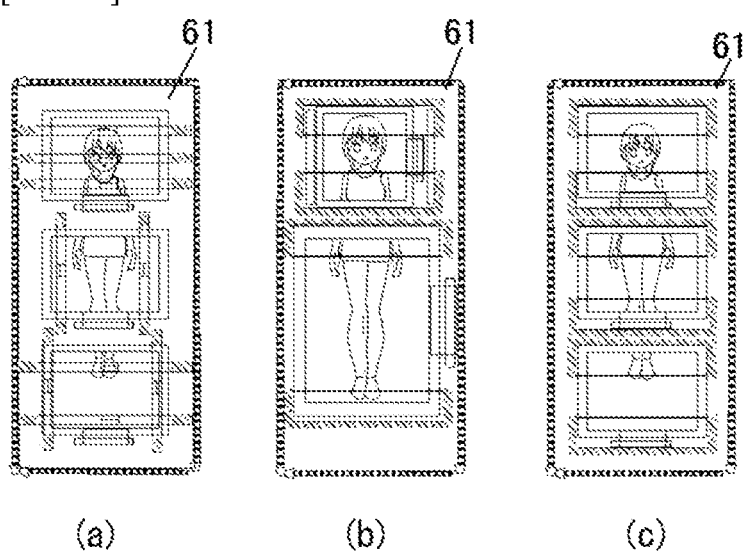
[FIG. 19]
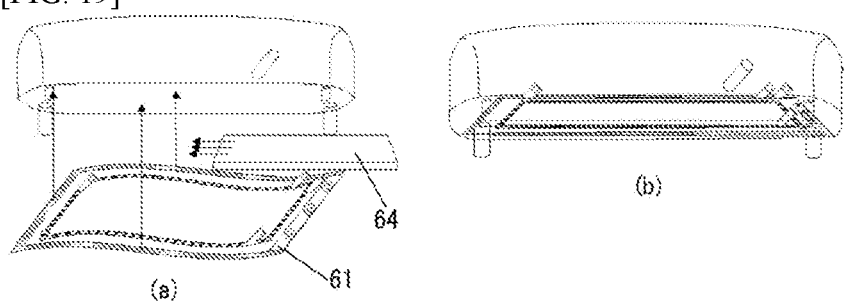
[FIG. 20]
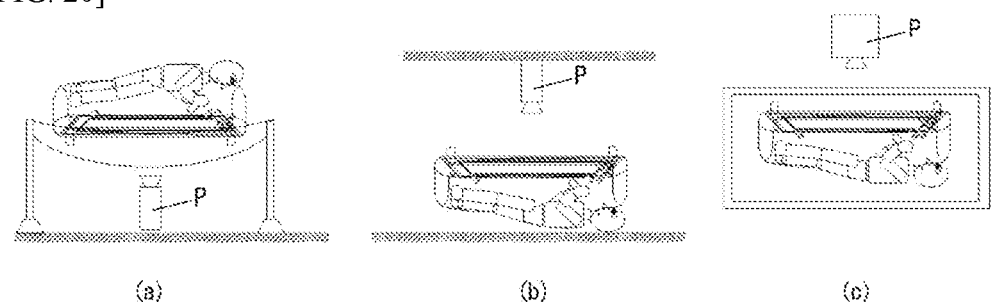

[FIG. 21]
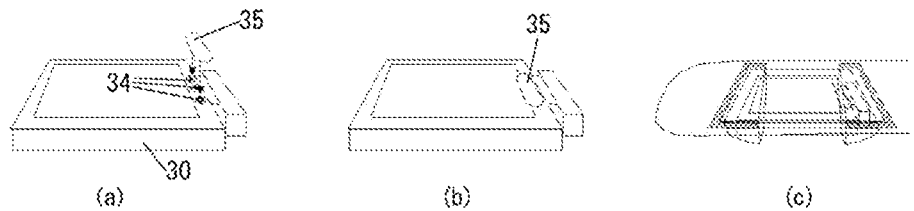
[FIG. 22]
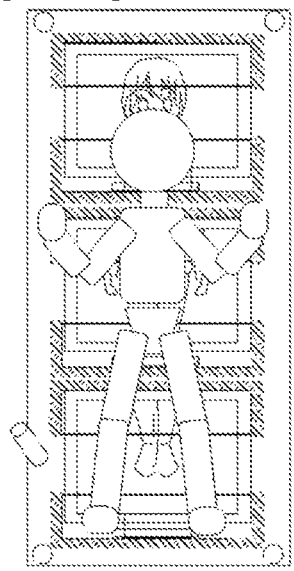
[FIG. 23]
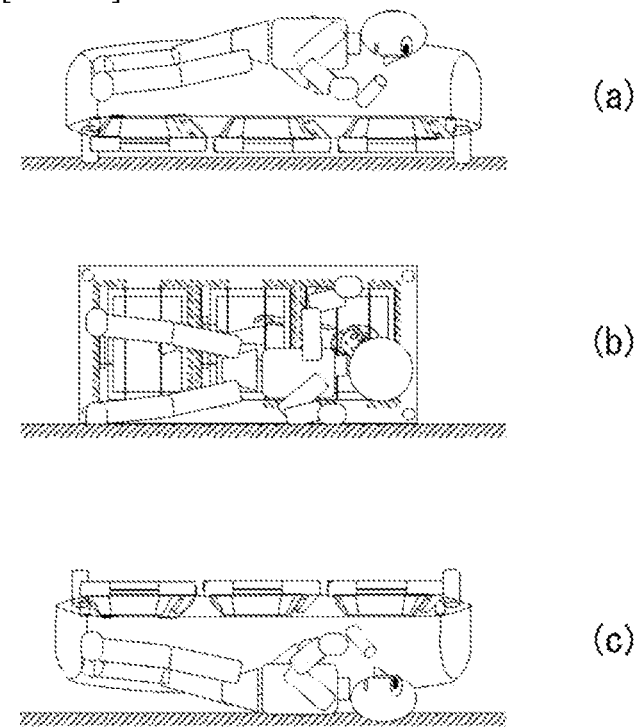
(a)
(b)
(c)

[FIG. 24]
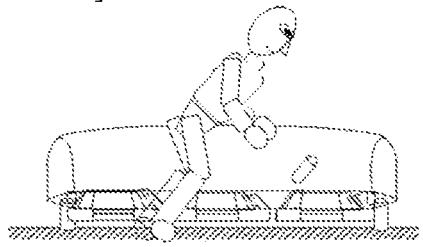
[FIG. 25]
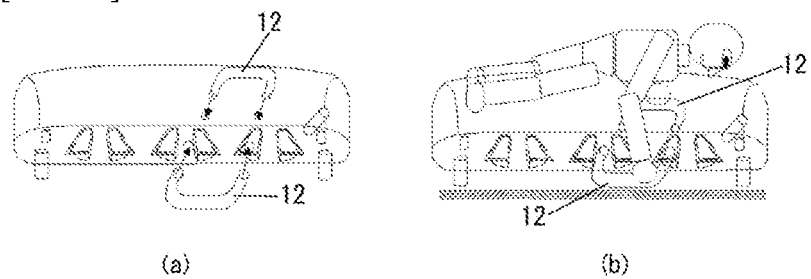
(a)  (b)
[FIG. 26]
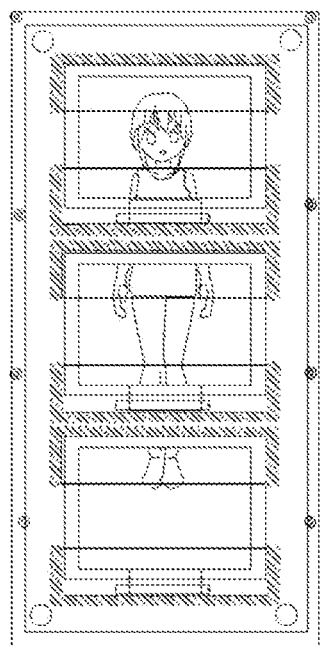
(a)
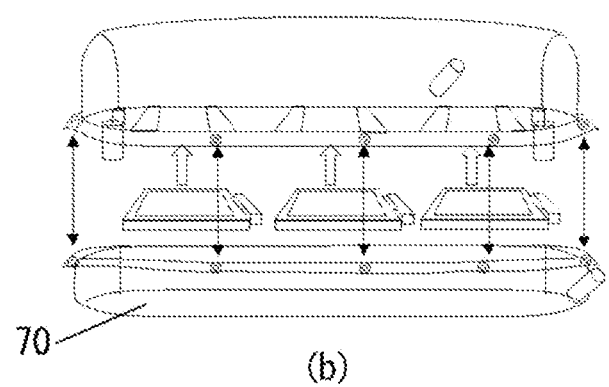
(b)
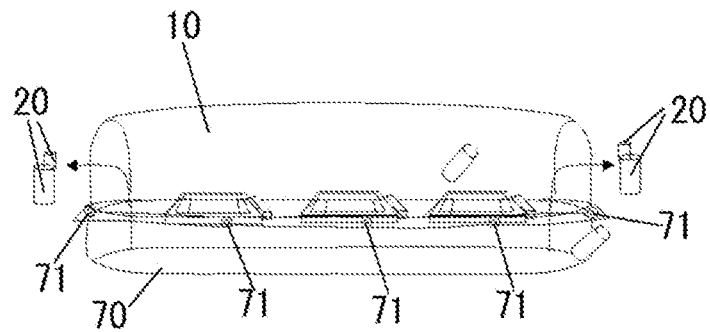
(c)

[FIG. 27]
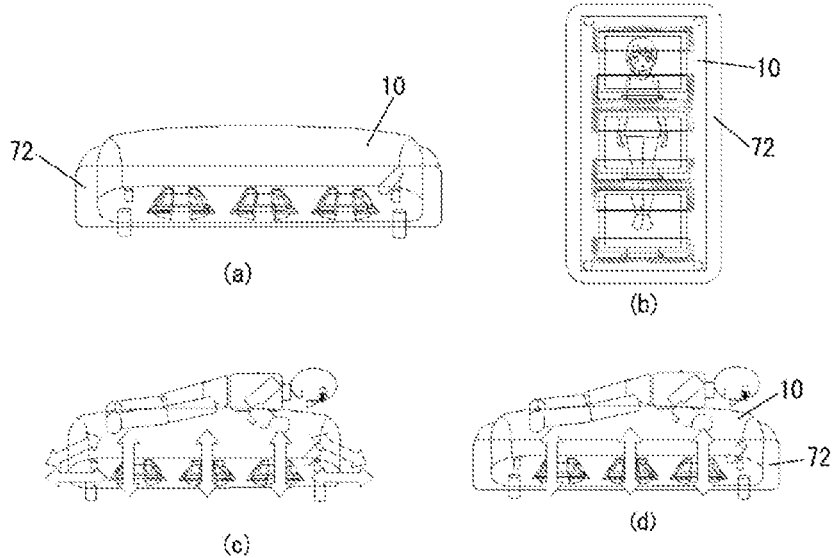
[FIG. 28]
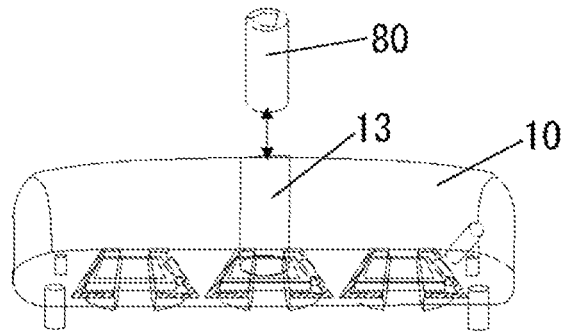
[FIG. 29]
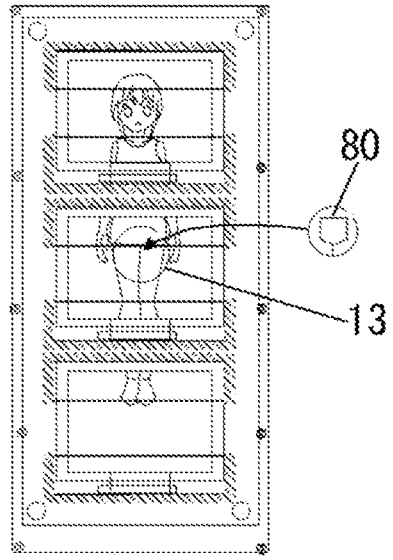

[FIG. 30]
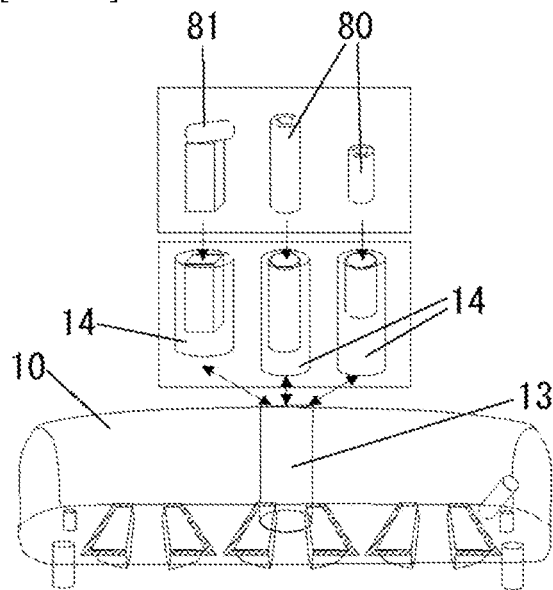
[FIG. 31]
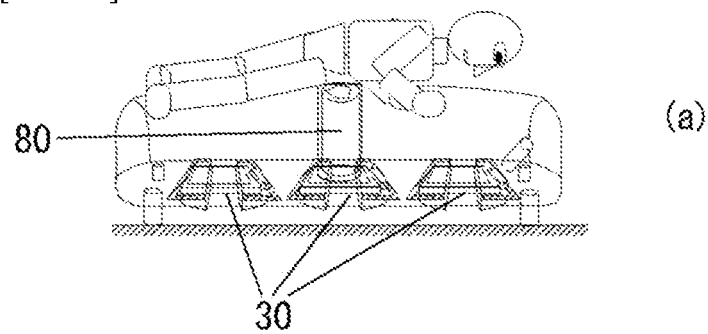
[FIG. 32]
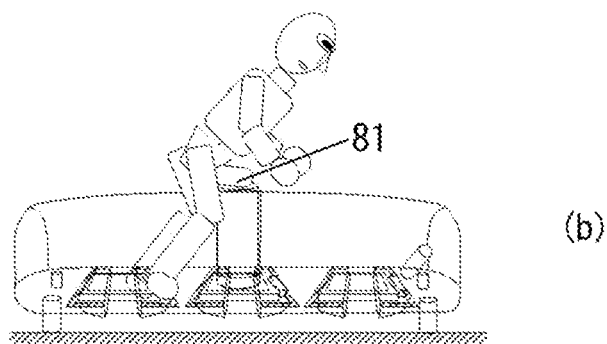

[FIG. 33]
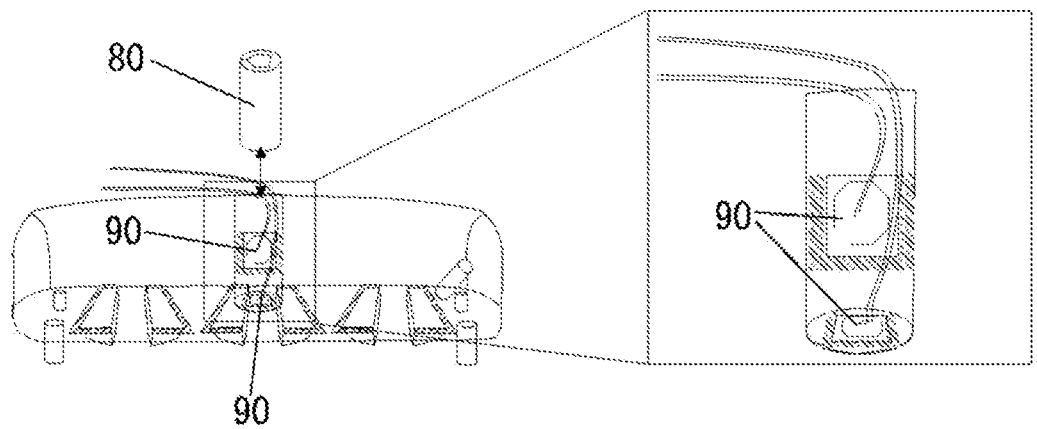
[FIG. 34]
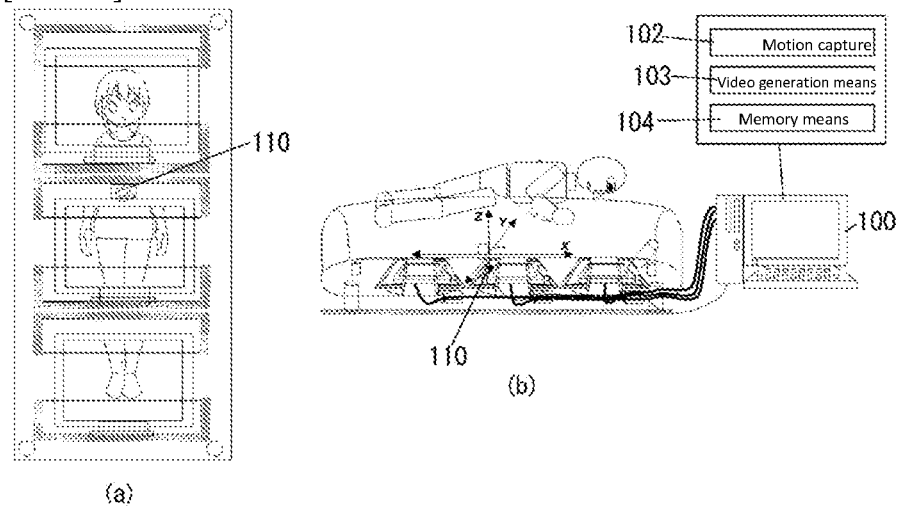
[FIG. 35]
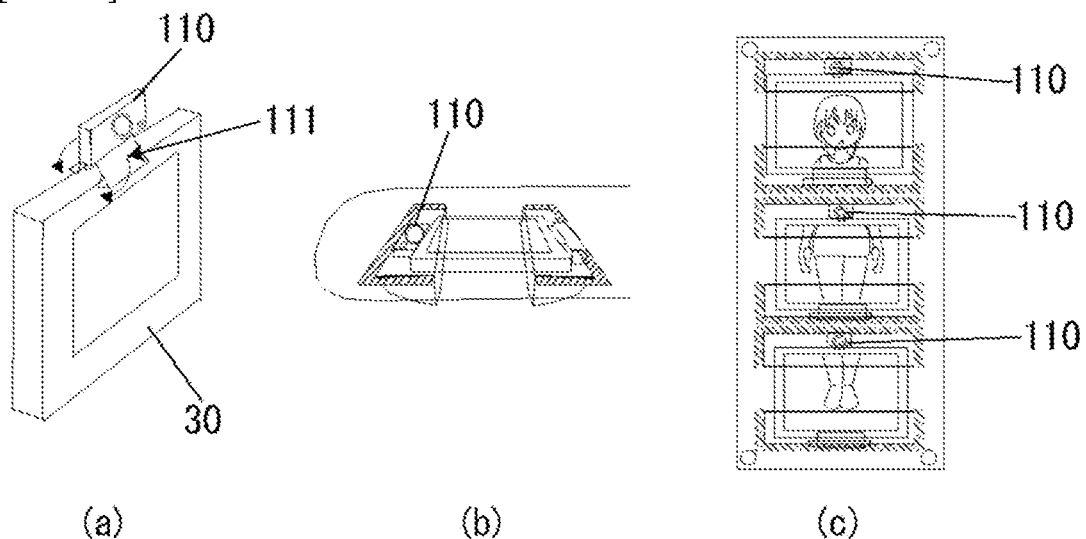

[FIG. 36]
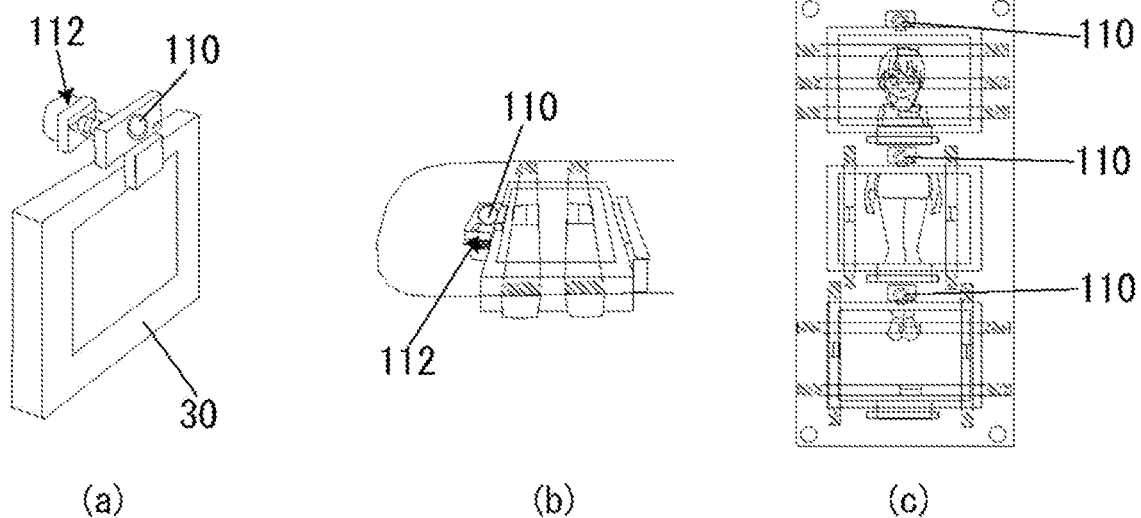
(a)　　　(b)　　　(c)
[FIG. 37]
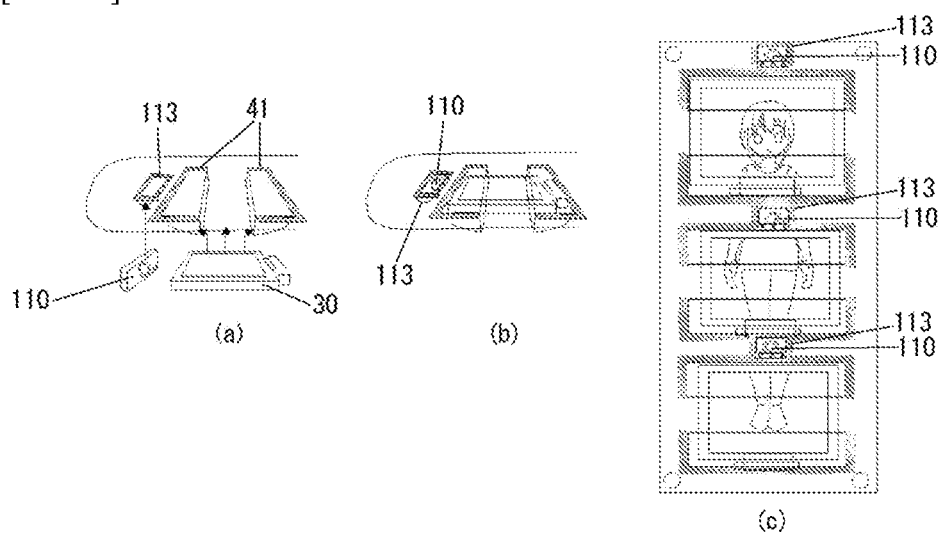
(a)　　　(b)　　　(c)

[FIG. 38]
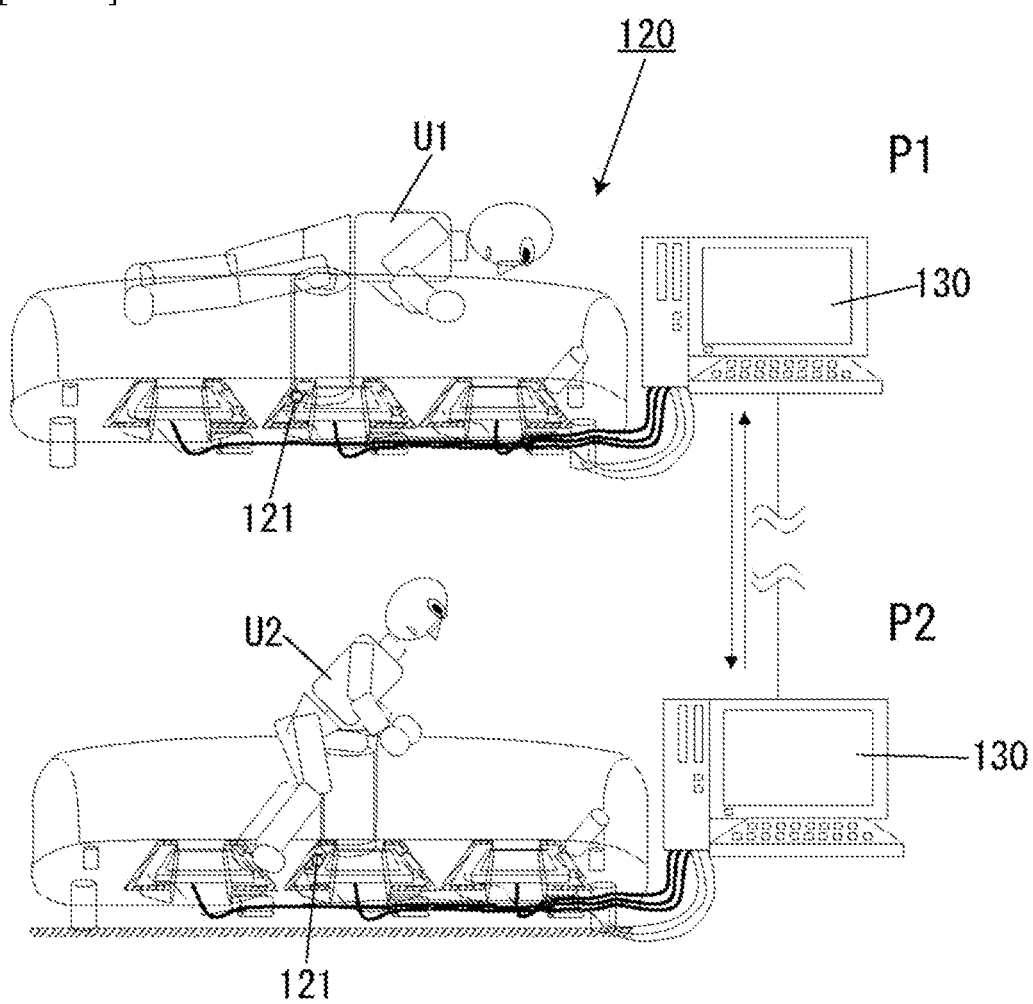

BODY PILLOW AND VIDEO COMMUNICATION SYSTEM

CROSS-REFERENCE TO RELATED APPLICATIONS

This application is the U.S. National Phase under 35 U.S.C. § 371 of International Application PCT/JP2017/022620, filed Jun. 20, 2017, which claims priority to Japanese Patent Application No. 2016-122561, filed Jun. 21, 2016. The International Application was published under PCT Article 21(2) in a language other than English.

TECHNICAL FIELD

The present invention relates to a body pillow which allows the user to view a video while hugging the pillow in various postures and which can also stimulate the user's body parts, as well as a video communication system using such body pillow.

BACKGROUND ART

Body pillows, etc., having images of persons printed on their surface are known. The user of a body pillow relaxes, feeling as if he/she were hugging his/her loved one (Patent Literatures 1 and 2).

Also known are semen collection apparatuses designed for medical treatment and research purposes (Patent Literatures 3 and 4). Semen collection apparatuses are widely used by medical institutions, etc., for better understanding of the workings of artificial insemination and causes of infertility, etc., while these apparatuses, when applied for personal use to satisfy one's sexual desire, are also known to prevent sex crime, prostitution, sexually transmitted disease, etc.

Also known are small hand-held massage devices designed to locally apply vibration to the user's body parts to promote blood circulation, help remove waste products from the body, relieve fatigue, etc. (Patent Literature 5).

The issue of sexual needs of disabled persons is drawing attention of late, which has led to the birth of, for example, an ejaculation assistance service to help men with cerebral palsy, intractable neurological diseases, muscular diseases, or other disabilities, who have difficulty ejaculating on their own (Non-patent Literature 1).

The aforementioned body pillows, semen collection apparatuses, small massage devices, etc., can be used for medical/research purposes, to satisfy the sexual desires of individuals, and also to solve the issue of sexual needs of disabled persons.

BACKGROUND ART LITERATURE

Patent Literature

Patent Literature 1: Japanese Utility Model Registration No. 3197671

Patent Literature 2: Japanese Patent Laid-open No. 2000-154481

Patent Literature 3: Japanese Patent No. 5261382

Patent Literature 4: Japanese Patent No. 5260866

Patent Literature 5: Japanese Patent Laid-open No. 2014-140427

Non-Patent Literature

Non-patent Literature 1: Non-patent Literature 1: White Hands Inc., Solving the Issue of "Sexual Needs of Disabled Persons" http://www.whitehands.jp/disability.html

SUMMARY OF THE INVENTION

Problems to be Solved by the Invention

However, the aforementioned prior arts present problems as explained below.

To be specific, a problem with the arts described in Patent Literatures 1 and 2 is that the user quickly gets tired of a printed image that does not change.

Also, the arts described in Patent Literatures 3 to 5 present a problem in that the user receives direct stimulation to his/her body parts, but not much visual stimulation. Also, the user is supposed to be sitting in a chair or otherwise assuming an upright position or lying face up on a bed, etc. As a result, these devices are difficult to use while lying face down, and this may create a challenge for disabled persons whose mobility is limited.

In light of the aforementioned problems, the present invention aims to provide a body pillow which allows the user to view a video while hugging the pillow in various postures such as lying face up, face down, or sideways, and which can also stimulate the user's body parts, as well as to provide a video communication system using such body pillow.

Means for Solving the Problems

The body pillow proposed by the present invention is characterized in that it comprises: a cushion part of hollow construction made of a transparent and flexible material; leg parts extending downward from the bottom face of the cushion part to create an air flow passage underneath the bottom face; and affixing means for affixing video playback devices to the bottom face of the cushion part with their video display surfaces facing up.

Also, the body pillow proposed by the present invention is characterized in that the affixing means are pockets in which the video playback devices are inserted.

Also, the body pillow proposed by the present invention is characterized in that the affixing means are belts that hold the video playback devices against the bottom face of the cushion part.

Also, the body pillow proposed by the present invention is characterized in that it has a reinforcement plate made of a transparent material, provided between the bottom face of the cushion part and the video playback devices.

Also, the body pillow proposed by the present invention is characterized in that it does not have leg parts and instead, a second cushion part filled with water is attached to the underside of the cushion part.

Also, the body pillow proposed by the present invention is characterized in that it has an outer skeletal part provided in a manner encasing the underside and side faces of the cushion part.

Also, the body pillow proposed by the present invention is characterized in that the top face of the cushion part has a concave part for storing a semen collection apparatus or small massage device.

Also, the body pillow proposed by the present invention is characterized in that it has: a piezoelectric element in the concave part; and a video generation means for generating, based on electrical signals generated by the piezoelectric element, a video of a person to be played on the video playback devices.

Also, the body pillow proposed by the present invention is characterized in that it has: a motion capture means for detecting, with a camera, movements of each part of the user watching a video on the video display surface from the top face of the cushion part, and then generating numerical coordinate data representing the detected movements of each part; and a video generation means for generating, based on the numerical coordinate data, a video of a person to be played on the video playback devices.

The video communication system proposed by the present invention is characterized in that: it has one aforementioned body pillow at a first location and another at a second location; each body pillow has a camera for capturing the user watching a video on the video display surface from the top face of the cushion part; and a video of the user at one location as captured by the camera is sent via an Internet line and played on the video playback devices for the user at the other location.

Effects of the Invention

The body pillow proposed by the present invention has video playback devices on the bottom face of the transparent cushion part, so the user can view a video in various postures such as lying face up, face down, or sideways.

Heat generated by the video playback devices can be released to the exterior through the space formed by the leg parts.

By using pockets or belts, the video playback device can be easily affixed to the bottom face of the cushion part, and changing the orientation of each video playback device also becomes easy.

By providing a reinforcement plate between the bottom face of the cushion part and the video playback devices, distortion of the video display surfaces can be prevented.

When a second cushion part is used instead of the leg parts, the video playback devices can be cooled by a water-cooling mechanism comprising the second cushion part filled with water.

When an outer skeletal part encasing the underside and side faces of the cushion part is used, deflection of the cushion part can be prevented.

When a concave part is provided in the top face of the cushion part and a semen collection apparatus or small massage device is stored therein, the user can view a video while receiving stimulation to his/her body parts.

Also, when a piezoelectric element is installed in the concave part to generate a video based on electrical signals generated by the piezoelectric element, or motion capture technology is used to generate a video according to how the user moves, performance of a virtual sexual act can be facilitated in a more interactive manner.

According to the video communication system proposed by the present invention, a video can be shared by the body pillows placed at the first and second locations, which enables a simulated sexual act to be performed from remote locations, helping a couple who are physically away from each other relieve stress and remain emotionally connected.

BRIEF DESCRIPTION OF THE DRAWINGS

FIG. 1 Plan view (a) and bottom view (b) of the body pillow in the first embodiment FIG. 2 Side view (a) of the body pillow, and side view (b) showing how it is used FIG. 3 Side views and longitudinal cross-sectional views (a) to (c) showing variation examples of body pillow shapes FIG. 4 Enlarged view of the structure of the leg part FIG. 5 Side views (a) to (c) showing variation examples of leg parts FIG. 6 Side views (a) and (b) showing variation examples of leg parts FIG. 7 Drawings (a) and (b) showing the pocket shape FIG. 8 Bottom views (a) and (b) and side view (c) showing examples of how the cables are wired FIG. 9 Side views (a) and (b) showing variation examples of pockets FIG. 10 Side views (a) and (b) showing the sheet shape FIG. 11 Plan views (a) to (d) showing examples of how the video playback devices are placed FIG. 12 Side views (a) and (b) and longitudinal cross-sectional view (c) showing the belt shape FIG. 13 Plan view showing the video playback devices affixed by the belts FIG. 14 Side views (a) and (b) and longitudinal cross-sectional view (c) showing the rubber belt shape FIG. 15 Side views (a) to (c) showing the reinforcement plate FIG. 16 Side views (a) and (b) showing a variation example of reinforcement plate FIG. 17 Side views (a) and (b) showing a variation example of sheet FIG. 18 Plan views (a) to (c) showing examples of how the video playback devices are placed FIG. 19 Side views (a) and (b) showing how a transmission-type projector screen is installed FIG. 20 Side views (a) and (b) and plan view (c) showing the body pillow with the transmission-type projector screen in use FIG. 21 Side views (a) to (c) showing the operation buttons covered with a protective sheet FIG. 22 Plan view showing the body pillow in use FIG. 23 Side views (a) to (c) showing the body pillow in use FIG. 24 Side view showing the body pillow in use FIG. 25 Side views (a) and (b) showing the attached handles FIG. 26 Plan view (a) and side views (b) and (c) showing the body pillow in the second embodiment, with a second cushion part attached FIG. 27 Side view (a) and plan view (b) with an outer skeletal part, side view (c) without an outer skeletal part, and side view (d) with an outer skeletal part, of the body pillow in the third embodiment FIG. 28 Side view showing the body pillow in the fourth embodiment, with a semen collection apparatus or small massage device stored in a concave part FIG. 29 Plan view showing the semen collection apparatus or small massage device stored in the concave part FIG. 30 Drawing showing examples of spacer shapes FIG. 31 Side views (a) and (b) showing the body pillow in use FIG. 32 Side view of the body pillow in the fifth embodiment, with a piezoelectric element installed in a concave part FIG. 33 Enlarged view showing how the piezoelectric element is installed FIG. 34 Plan view (a) and side view (b) of the body pillow in the sixth embodiment, with a camera attached FIG. 35 Drawing (a), side view (b) and plan view (c) of cameras, each affixed with a spring to a video playback device FIG. 36 Drawing (a), side view (b) and plan view (c) of cameras, each affixed to a video playback device with a clamp FIG. 37 Side view (a), side view (b) and plan view (c) of cameras, each affixed to the cushion part using pockets FIG. 38 Drawing showing the configuration of a video communication system

MODE FOR CARRYING OUT THE INVENTION

First Embodiment

The body pillow proposed by the present invention is explained below using the drawings.

As shown in FIGS. 1 and 2, the body pillow 1 roughly comprises a cushion part 10, leg parts 20, video playback devices 30, and affixing means 40.

The cushion part 10 is of hollow construction, formed by a transparent and flexible material. The shape of the cushion part 10 is not limited in any way so long as the video playback devices 30 can be affixed to its bottom face, but it may be rectangular solid, semi-cylindrical, or semi-circular, for example, as shown in FIG. 3.

An example of the transparent and flexible material includes, but is not limited to, soft vinyl chloride. Air is filled into the cushion part 10 via an inlet 11, but other substances such as water or other clear liquid, or clear gel, may be filled instead.

The dimensions of the cushion part 10 are not limited in any way; in this embodiment, however, the overall length of the cushion part 10 is greater than the height of the user.

The leg parts 20 are members extending downward from the bottom face of the cushion part 10. In this embodiment, a total of four leg parts 20 are provided at the four corners of the bottom face of the cushion part 10; however, more than four such parts may be provided to increase the bearing load in consideration of the weight of the user, weight of the video playback devices 30, etc.

To be specific, the leg part 20 comprises a large female thread 21 and a male screw 22, as shown in FIG. 4.

With the head part 21a of the female thread 21 contacting the bottom face of the cushion part 10, and the shaft 21b of the female thread 21 guided through the opening in a sheet 23, the sheet 23 is joined to the bottom face of the cushion part 10 by any known joining means such as adhesive, thermal compression bonding, thermal fusion using high-frequency current, or the like (the joined locations are shaded in FIG. 4; the same applies in other drawings). Then, by binding the sheet 23 around the shaft 21b with O-rings 24, the leg part 20 is affixed to the cushion part 10.

The head part 22a of the male screw 22 is contacting the floor surface, and the height of the leg part 20 is adjusted by turning the male screw 22, which is engaged with the female thread 21, around the shaft. It should be noted that the female thread 21 may be positioned on the bottom side (side contacting the floor surface) and the male screw 22, on the top side.

The leg parts 20 provide a space between the cushion part 10 and the floor surface, and this space is used as an air flow passage S. Heat generated by the video payback devices 30 is released to the exterior through the air flow passage S.

It should be noted that the leg parts 20 may be constituted in a manner shown in FIG. 5, where a base 25 having two threaded holes 25a, one on the left side and the other on the right side, is affixed to the bottom face of the cushion part 10 using multiple belts 26, and then first male screws 27a are screwed into the threaded holes 25a, after which second male screws 27b are screwed into the threaded holes 25a provided at the bottom faces of the first male screws 27a. In this case, the second male screw 27b is turned around the shaft to adjust the height of the leg part 20. A cushion material may be wrapped around the first male screw 27a and second male screw 27b.

Also, as shown in FIG. 6, U-shaped leg parts 28 may be installed on the left side and the right side. By making the U-shaped leg parts 28 hollow and integrally forming them with the cushion part 10 so that they connect continuously to the cushion part 10, the comfort of using the body pillow will increase because the U-shaped leg parts 28 have elasticity. It should be noted that the U-shaped leg parts 28 may be made solid and provided separately from the cushion part 10.

The video playback devices 30 are devices for showing a video to the user, and are affixed to the bottom face of the cushion part 10 with their video display surfaces 31 facing up.

It suffices that the video playback devices 30 are flat, and TVs, monitors, tablet terminals, etc., using liquid crystal displays or organic electroluminescent displays may be used, for example.

The affixing means 40 are members for affixing the video playback devices 30 to the bottom face of the cushion part 10, and pockets 41 are used in this embodiment.

The pocket 41 is a bag extending in the lateral direction, with one long-direction side open. As shown in FIG. 7, the top faces of two pockets 41 spaced in the longitudinal direction are joined to the bottom face of the cushion part 10 by any known joining means such as adhesive, thermal compression bonding, thermal fusion using high-frequency current, or the like, and then the front end and back end of the video playback device 30 are inserted into the respective pockets 41, to affix the video playback device 30.

By providing slits 42 in the pockets 41, heat generated by the video playback device 30 can be more effectively directed downward to be released to the exterior through the air flow passage S.

As shown in FIG. 8, the video playback device 30 may have power, HDMI (registered trademark), and other cables 32 connected to it, in which case these cables 32 can be guided through the openings of the pockets 41 or slits 42 therein, and bundled with tie-bands 33.

In this embodiment, three video playback devices 30 are affixed to the bottom face of the cushion part 10, and as shown in FIG. 1, the top part, center part, and bottom part of a person can be projected onto the three video display surfaces 31, respectively, to project a video of an almost life-size person.

Lying face down and hugging the body pillow 1, the user U can watch the video of an almost life-size person on the video display surfaces 31 through the transparent cushion part 10.

It should be noted that, as shown in FIG. 9, filler materials 43 whose shape corresponds to the interior shape of the pocket 41 may be formed by rubber, urethane or other flexible, low-resilience material. By forming tenons 43a and heat-radiating slits 43b on the side faces of the filler materials 43 that receive the front end and back end of the video playback device 30, the video playback device 30 can be affixed more securely, and also the corners of the video playback device 30 will not scratch or make holes in the cushion part 10.

As shown in FIG. 10, the entire bottom face of the video playback device 30 can be covered with a large sheet 44, instead of using pockets 41. In this case, it suffices that three of the four sides of the sheet are joined to the bottom face of the cushion part 10, with the remaining side secured with hooks 45, fasteners, buttons, hook-and-loop fastener, etc. Preferably the sheet 44 has slits 46 for radiating heat.

The number of video playback devices 30 affixed to the body pillow 1 is not limited in any way, so long as there is at least one such device. In FIG. 11 (*a*), three video playback devices 30 are affixed in such a way that the longitudinal direction is a lateral direction using pockets 41, with the length direction of their video display surfaces 31 corresponding to the lateral direction. In FIG. 11 (*b*), three video playback devices 30 are affixed in such a way that the longitudinal direction is an anteroposterior direction using pockets 41, with the length direction of their video display surfaces 31 corresponding to the longitudinal direction. In this case, the gaps created on the left and right sides of the pockets 41 are filled with spacers 47 to prevent each video playback device 30 from shifting. In FIG. 11 (*c*), three video playback devices 30 are affixed in such a way that the longitudinal direction is a lateral direction using a large sheet 44, with the length direction of their video display surfaces 31 corresponding to the lateral direction. In this case, the gaps created between the adjacent video playback devices 30 are filled with spacers 47. In FIG. 11 (*d*), two video playback devices 30 are affixed in such a way that the longitudinal direction is an anteroposterior direction using pockets 41, with the length direction of their video display surfaces 31 corresponding to the longitudinal direction. By changing the pocket 41 sizes and the spacing between each pair of pockets 41, two video display surfaces 31 of different dimensions can be accommodated.

As shown in FIG. 12, belts 48 that hold the video display device 30 against the bottom face of the cushion part 10 may be used as the affixing means 40.

Each belt 48 consists of a set of two belt halves, where one end of one belt half 48 is joined to the right side of the bottom face of the cushion part 10, while one end of the other belt half 48 is joined to the left side of the bottom face of the cushion part 10. Then, the other ends of the two belt halves 48 are tied together using a buckle 48*a* or other known fastening means, to hold the video display device 30 against, and thereby affix it to, the bottom face of the cushion part 10. In FIG. 13, two or three belt sets are used for one video playback device 30. Also, rubber belts 49 having elasticity may be used, as shown in FIG. 14.

As shown in FIG. 15, a reinforcement plate 50 made of acrylic, polycarbonate, or other transparent material may be installed between the bottom face of the cushion part 10 and the video playback device 30. Although the video display surfaces 31 are protected by the air, water, etc., filled in the cushion part 10, installing the reinforcement plate 50 can increase withstand load.

As shown in FIG. 16, the reinforcement plate 50 may be large enough to cover the entire bottom face of the cushion part 10. Installing a large reinforcement plate 50 allows the multiple video display surfaces 31 to be positioned in the same plane without warping, which makes it easy to watch the video. Also, as shown in FIG. 17, a sheet 60 to which multiple pockets 41 are joined may be joined, via fasteners 62, etc., to the bottom face of a sheet 61 which is larger than this sheet 60, and a reinforcement plate 50 may be inserted between the large sheet 61 and the bottom face of the cushion part 10. It suffices that three sides of the large sheet 61 are joined, with the remaining side secured with a fastener 63, etc. As shown in FIG. 18, multiple sheets 61 having pockets 41 at different positions may be prepared and used selectively as deemed appropriate to change the layout of video playback devices 30. Also, instead of installing the sheet 60 with pockets 41 joined to it, a transmission-type screen 64 attached to a transparent plate may be inserted over the large sheet 61, as shown in FIG. 19, so that the light from an external projector P can be projected onto the transmission-type screen 64 for viewing by the user, as shown in FIG. 20.

As shown in FIG. 21, the operation buttons 34 on the video playback device 30 may be covered with a protective sheet 35, in order to prevent accidental pressing of the operation buttons during use.

As shown in FIGS. 22 to 24, the user can view the video while lying face down, sideways, or face up, or straddling. As shown in FIG. 25, handles 12 may be provided on the left and right sides of the cushion part 10 to help stabilize the posture of the user during viewing.

Second Embodiment

The second embodiment of the present invention is explained, where locations constituted in the same way as the corresponding locations in the aforementioned first embodiment are denoted by the same symbols and are not explained.

As shown in FIG. 26, the body pillow of this embodiment is characterized in that the leg parts 20 are removed and a second cushion part 70 is installed on the underside of the cushion part 10. It suffices that the cushion part 10 and second cushion part 70 are installed using hooks 71, fasteners, or other known joining means. Filling the second cushion part 70 with water provides a so-called water-cooling mechanism because the water absorbs the heat from the video playback devices 30, and the heat radiation efficiency increases as a result.

Third Embodiment

The third embodiment of the present invention is explained, where locations constituted in the same way as the corresponding locations in each of the aforementioned embodiments are denoted by the same symbols and are not explained.

As shown in FIG. 27, the body pillow in this embodiment is characterized in that it has an outer skeletal part 72 encasing the underside and side faces of the cushion part 10.

The outer skeletal part 72 is shaped like a box having an opening at the top, and its inside dimensions are such that the cushion part 10 can be accommodated with virtually no gaps left around it. Installing the outer skeletal part 72 prevents the cushion part 10 from deflecting in the longitudinal and lateral directions as indicated by the arrows, which helps stabilize the posture of the user and also prevents each video playback device 30 from warping. The outer skeletal part may be made of urethane or other material having appropriate cushion property.

Fourth Embodiment

The fourth embodiment of the present invention is explained, where locations constituted in the same way as the corresponding locations in each of the aforementioned embodiments are denoted by the same symbols and are not explained.

As shown in FIGS. 28 to 30, the body pillow in this embodiment is characterized in that it has a concave part 13 in the top face of the cushion part 10 for storing a semen collection apparatus 80 or small massage device 81.

The concave part 13 in this embodiment is a hole penetrating through the cushion part 10 from the top face to the bottom face, and a semen collection apparatus 80 or small massage device 81 is inserted in this hole. Spacers 14 are tubular members made from urethane or other low-resilience material, and as shown in FIG. 30, several types of such spacers having different thicknesses may be prepared. These spacers 14 can be used selectively as deemed appropriate according to the size of the concave part 13 and the size of the semen collection apparatus 80 or small massage device 81. Once fit in the concave part 13, the spacer 14 is securely held in place by the pressure from the surrounding wall and does not easily shift during use. The spacer 14 may also be completely affixed to the concave part 13 using a hook-and-loop fastener, hooks, etc. The concave part 13 need not penetrate the cushion part 10 from top to bottom, and it may be sufficient to concave only the top face of the cushion part 10.

FIG. 31 (a) shows a man using the body pillow, while FIG. 31 (b) shows a woman using the body pillow. The three video playback devices 30 are playing, for example, a video of a life-size person of different sex, respectively, and each user can view the video and stimulate his/her body parts using the semen collection apparatus 80 or small massage device 81 while lying face down or straddling. Needless to say, the body pillow can also be used while lying face up or sideways.

Fifth Embodiment

The fifth embodiment of the present invention is explained, where locations constituted in the same way as the corresponding locations in each of the aforementioned embodiments are denoted by the same symbols and not explained.

As shown in FIGS. 32 and 33, the body pillow in this embodiment is characterized in that it has: a piezoelectric element 90 in the concave part 13; and a video generation means 101 for generating, based on electrical signals generated by the piezoelectric element 90, a video of a person to be played on the video playback devices 30.

To be specific, the semen collection apparatus 80 is inserted into the concave part 13 with the piezoelectric element 90 joined to the inner periphery face or underside of the concave part 13. While the body pillow is in use, the semen collection apparatus 80 moves/expands in the longitudinal, lateral and vertical directions, and the piezoelectric element 90 detects these movements/expansions and sends electrical signals to the video generation means 101 inside the computer 100. The video generation means 101 receives and analyzes the electrical signals in real time, and generates a video according to the movements/expansions and plays it on the video playback devices 30.

Sixth Embodiment

The sixth embodiment of the present invention is explained, where locations constituted in the same way as the corresponding locations in each of the aforementioned embodiments are denoted by the same symbols and are not explained.

As shown in FIG. 34, the body pillow in this embodiment is characterized in that it has: a motion capture means 102 for detecting, with a small camera (web camera, etc.) 110, movements of each part of the user watching a video on the video display surface 31 from the top face of the cushion part 10, and then generating numerical coordinate data representing the detected movements of each part; and a video generation means 103 for generating, based on the numerical coordinate data, a video of a person to be played on the video playback devices 30.

As shown in FIGS. 35 and 36, one or more small cameras 110 is/are affixed to a part(s) of each video playback device 30 using a spring(s) 111 or clamp(s) 112. It should be noted that, as shown in FIG. 37, pockets 113 for storing each such small camera may be provided separately.

The user's video data captured by the small camera 110 is loaded into the motion capture means 102 in the computer 100. The video data may include audio data.

The motion capture means 102 matches the loaded video data to appropriate pattern data among the pattern data comprising still images, videos, etc., representing various features of the human body that are pre-stored in the memory means 104 in the computer 100. Then, the motion capture means 102 recognizes each part of the user, such as head, arm, leg, hand, fingertip, etc., from the user's image, and calculates the movements of each part as XYZ numerical coordinate data.

In the memory means 104 in the computer 100, numerical coordinate data of the head, arm, leg, hand, fingertip and other parts of a life-size virtual model are pre-stored.

The video generation means 103 in the computer 100 compares the numerical coordinate data relating to the head, arm, leg, hand, fingertip and other parts of the user as calculated by the motion capture means 102, against the numerical coordinate data of the head, arm, leg, hand, fingertip and other parts of the life-size virtual model stored in the memory means 104.

Then, if the XYZ coordinates of a given part of the user matches the XYZ coordinates of a given part of the virtual model, the video generation means 103 recognizes that the user is touching the virtual model at the applicable parts, generates a video of the life-size virtual model by reflecting this information, and outputs the video to the multiple video playback devices 30.

It should be noted that the processing performed by the video generation means 103 is based on a general known processing method called "collision detection" or "hit test." One possible method to reduce the processing load is to fix the Z-coordinate and assume that the user is always touching the virtual model along the Z-coordinate, thereby omitting some of the hit test processing in the interest of processing speed.

It should be noted that the processing performed by the motion capture means 102 and video generation means 103, as described above, are examples of interactive processing that simulates the user touching the life-size virtual model played on the video playback devices 30. Besides the above, any simple processing method may be adopted, such as one that causes the virtual model to change its facial expression when a movement of the user's right hand is sensed, for example.

The video communication system proposed by the present invention is explained.

As shown in FIG. 38, the video communication system 120 is characterized in that: it has one aforementioned body pillow 1 at a first location P1 and another at a second location P2; each body pillow 1 has one or more small cameras 121 for capturing the user watching a video on the video display surface 31 from the top face of the cushion part 10; and a video of the user U1 at one location P1 as captured by the small camera(s) 121 is sent via the Internet connection and played on the video playback devices 30 for the user U2 at the other location P2.

To be specific, each such small camera 121 is installed on one of the video playback devices 30 of the body pillow for the user U1 at the first location P1, and video data captured by this small camera 121 is loaded into the computer 130. The video data is then compressed, securely encrypted and/or processed by other known methods, and finally converted to packet data and sent via the Internet to the computer 130 for the other user U2 at the second location P2.

The computer 130 for the other user U2 extracts, decrypts and/or processes the received video data by other known methods, including processing for multi-display presentation according to the size, orientation, etc., of each of the multiple video playback devices 30, and plays the result on the multiple video playback devices 30. This video data may include audio data.

The same thing happens on the other user U2 side, with video data of the other user U2 sent to the user U1 and played on the multiple video playback devices 30 for the user U1.

According to this video communication system 120, a sexual act can be simulated from remote locations by, for example, installing a male masturbation apparatus 80 on one body pillow and a female massage device 81 on the other body pillow.

INDUSTRIAL FIELD OF APPLICATION

The present invention relates to a body pillow which allows the user to view a video in various postures and which can also stimulate the user's body parts, as well as a video communication system using such body pillow, and both have potential industrial applications.

DESCRIPTION OF THE SYMBOLS

P Projector
P1 First location
P2 Second location
S Air flow passage
U User
1 Body pillow
10 Cushion part
11 Inlet
12 Handle
13 Concave part
14 Spacer
20 Leg part
21 Female thread
21a Head part
21b Shaft
22 Male screw
22a Head part
23 Sheet
24 O-ring
25 Base
25a Threaded hole
26 Belt
27a First male screw
27b Second male screw
28 U-shaped leg part
30 Video playback device
31 Video display surface
32 Cable
33 Tie-band
34 Operation button
35 Protective sheet
40 Affixing means
41 Pocket
42 Slit
43 Filler material
43a Tenon
43b Slit
44 Large sheet
45 Hook
46 Slit
47 Spacer
48 Belt
48a Buckle
49 Rubber belt
50 Reinforcement plate
60 Sheet
61 Large sheet
62 Fastener
63 Fastener
64 Transmission-type screen
70 Second cushion part
71 Hook
72 Outer skeletal part
80 Semen collection apparatus
81 Small massage device
90 Piezoelectric element
100 Computer
101 Video generation means
102 Motion capture means
103 Video generation means
104 Memory means
110 Small camera
111 Spring
112 Clamp
113 Pocket
120 Video communication system
121 Small camera
130 Computer

What is claimed is:

1. A body pillow, characterized by comprising: a cushion part of hollow construction made of a transparent and flexible material; leg parts extending downward from a bottom face of the cushion part to create an air flow passage underneath the bottom face; and affixing means for affixing video playback devices to the bottom face of the cushion part with video display surfaces of the video playback devices facing up.

2. The body pillow according to claim 1, characterized in that the affixing means are pockets in which the video playback devices are inserted.

3. The body pillow according to claim 2, characterized by further comprising a reinforcement plate made of a transparent material, provided between the bottom face of the cushion part and the video playback devices.

4. The body pillow according to claim 2, characterized by further comprising an outer skeletal part provided in a manner encasing an underside and side faces of the cushion part.

5. The body pillow according to claim 2, characterized in that a top face of the cushion part has a concave part for storing a semen collection apparatus or small massage device.

6. The body pillow according to claim 2, characterized by further comprising: a motion capture means for detecting, with a camera, movements of each part of a user watching a video on any of the video display surfaces from a top face of the cushion part, and then generating numerical coordinate data representing detected movements of each part; and a video generation means for generating, based on the numerical coordinate data, a video of a person to be played on the video playback devices.

7. A video communication system, characterized in that: the body pillow according to claim 2 is provided at a first location and another body pillow according to claim 2 at a second location; each body pillow has a camera for capturing a user watching a video on any of the video display surfaces from a top face of the cushion part; and a video of the user at one location as captured by the camera is sent via an Internet line and played on the video playback devices for the user at the other location.

8. The body pillow according to claim 1, characterized in that the affixing means are belts that hold the video playback devices against the bottom face of the cushion part.

9. The body pillow according to claim 8, characterized by further comprising a reinforcement plate made of a transparent material, provided between the bottom face of the cushion part and the video playback devices.

10. The body pillow according to claim 8, characterized by further comprising an outer skeletal part provided in a manner encasing an underside and side faces of the cushion part.

11. The body pillow according to claim 8, characterized in that a top face of the cushion part has a concave part for storing a semen collection apparatus or small massage device.

12. The body pillow according to claim 1, characterized by further comprising a reinforcement plate made of a transparent material, provided between the bottom face of the cushion part and the video playback devices.

13. The body pillow according to claim 1, characterized by further comprising an outer skeletal part provided in a manner encasing an underside and side faces of the cushion part.

14. The body pillow according to claim 13, characterized in that the affixing means are belts that hold the video playback devices against the bottom face of the cushion part.

15. The body pillow according to claim 1, characterized in that a top face of the cushion part has a concave part for storing a semen collection apparatus or small massage device.

16. The body pillow according to claim 15, characterized by further comprising: a piezoelectric element in the concave part; and a video generation means for generating, based on electrical signals generated by the piezoelectric element, a video of a person to be played on the video playback devices.

17. The body pillow according to claim 1, characterized by further comprising: a motion capture means for detecting, with a camera, movements of each part of a user watching a video on any of the video display surfaces from a top face of the cushion part, and then generating numerical coordinate data representing detected movements of each part; and a video generation means for generating, based on the numerical coordinate data, a video of a person to be played on the video playback devices.

18. A video communication system, characterized in that: the body pillow according to claim 1 is provided at a first location and another body pillow according to claim 1 at a second location; each body pillow has a camera for capturing a user watching a video on any of the video display surfaces from a top face of the cushion part; and a video of the user at one location as captured by the camera is sent via an Internet line and played on the video playback devices for the user at the other location.

19. A body pillow, characterized by comprising: a cushion part of hollow construction made of a transparent and flexible material; a second cushion part filled with water which is attached to an underside of the cushion part; and affixing means for affixing video playback devices to a bottom face of the cushion part with video display surfaces of the video playback devices facing up.

20. The body pillow according to claim 19, characterized in that the affixing means are pockets in which the video playback devices are inserted.

* * * * *